US012036516B2

(12) United States Patent
Choi et al.

(10) Patent No.: US 12,036,516 B2
(45) Date of Patent: Jul. 16, 2024

(54) METHOD OF CONTROLLING STRUCTURE OF DEFECTS IN MFI ZEOLITE MEMBRANES

(71) Applicant: KOREA UNIVERSITY RESEARCH AND BUSINESS FOUNDATION, Seoul (KR)

(72) Inventors: Jungkyu Choi, Seoul (KR); Kwan Young Lee, Seoul (KR); Sung-Won Hong, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 192 days.

(21) Appl. No.: 17/148,699

(22) Filed: Jan. 14, 2021

(65) Prior Publication Data

US 2021/0213396 A1 Jul. 15, 2021

(30) Foreign Application Priority Data

Jan. 15, 2020 (KR) .................. 10-2020-0005589

(51) Int. Cl.
*B01D 71/02* (2006.01)
*B01D 67/00* (2006.01)
*B01D 69/10* (2006.01)
*C07B 63/00* (2006.01)
(Continued)

(52) U.S. Cl.
CPC .... *B01D 71/0281* (2022.08); *B01D 67/00411* (2022.08); *B01D 69/107* (2022.08);
(Continued)

(58) Field of Classification Search
CPC ...... B01D 71/028; B01D 69/10; C07B 63/00; C07C 7/144; C07C 15/08
See application file for complete search history.

(56) References Cited

U.S. PATENT DOCUMENTS 5,672,388 A * 9/1997 McHenry ............... C23C 16/40
427/248.1
5,681,789 A   10/1997 Saxton et al.
(Continued)

FOREIGN PATENT DOCUMENTS

DE   695 33 510 T2   9/2005
JP   10-502573 A     3/1998
JP   2010-180080 A   8/2010

OTHER PUBLICATIONS

Korean Notice of Allowance issued on Jan. 14, 2021 in counterpart Korean Patent Application No. 10-2020-0005589 (5 pages in Korean).
(Continued)

*Primary Examiner* — Youngsul Jeong
(74) *Attorney, Agent, or Firm* — NSIP Law

(57) ABSTRACT

The present invention relates to a method of controlling a defect structure in an MFI zeolite membrane and a method of separating xylene isomers using the MFI zeolite membrane produced by the method, and more particularly, to a method of controlling a defect structure in an MFI zeolite membrane that improves the performance of separating a xylene isomer by reducing the amount and size of defects formed in the MFI membrane structure when removing organic-structure-directing agents in the membrane through calcination at a low temperature using ozone.

5 Claims, 5 Drawing Sheets

(51) Int. Cl.
C07C 7/14 (2006.01)
C07C 7/144 (2006.01)
C07C 15/08 (2006.01)

(52) U.S. Cl.
CPC ............ B01D 69/108 (2022.08); C07B 63/00 (2013.01); C07C 7/144 (2013.01); *B01D 2323/081* (2022.08); *B01D 2323/2181* (2022.08); *C07C 15/08* (2013.01)

(56) References Cited

U.S. PATENT DOCUMENTS

2007/0045174 A1    3/2007   Yeung et al.
2019/0366274 A1*   12/2019  Gu ........................ B01D 53/228

OTHER PUBLICATIONS

Choi, Jungkyu, et al., "MFI zeolite membranes from a-and randomly oriented monolayers," *Adsorption*, 12, 5-6, 2006 (pp. 339-360).

Choi, Jungkyu, et al., "Grain Boundary Defect Elimination in a Zeolite Membrane by Rapid Thermal Processing," *Science*, 325, 5940, 2009 (pp. 590-593).

Zhang, Yanfeng, et al., "Blocking defects in SAPO-34 membranes with cyclodextrin," *Journal of Membrane Science*, 358 1-2, 2010 (pp. 7-12).

Maghsoudi, Hafez., "Defects of zeolite membranes: Characterization, modification and post-treatment techniques," *Separation & Purification Reviews*, 45, 3, 2016 (pp. 169-192).

Zhu, Bo, et al., "A method for defect repair of MFI-type zeolite membranes by multivalent ion infiltration," *Microporous and Mesoporous Materials*, 237, 2017 (pp. 140-150).

Japanese Notice of Allowance issued on Jul. 28, 2022, in counterpart Japanese Patent Application No. 2021-004715 (2 Pages in English, 3 Pages in Japanese).

Heng, Samuel, et al. "Low-temperature ozone treatment for organic template removal from zeolite membrane." Journal of Membrane Science 243.1-2 (2004): 69-78.

German Office Action issued on Sep. 29, 2023, in counterpart German Patent Application No. 10 2021 200 256.0 (5 pages in English, 5 pages in German).

* cited by examiner

METHOD OF CONTROLLING STRUCTURE OF DEFECTS IN MFI ZEOLITE MEMBRANES

CROSS-REFERENCE TO RELATED APPLICATIONS

This application claims the benefit under 35 USC § 119(a) of Korean Patent Application No. 10-2020-0005589, filed on Jan. 15, 2020, the entire disclosure of which is incorporated herein by reference for all purposes.

TECHNICAL FIELD

The present invention relates to a method of controlling a defect structure in an MFI zeolite membrane. More particularly, the present invention relates to a method of controlling a defect structure in an MFI zeolite membrane that improves the performance of separating xylene isomers by reducing the amount and size of defects formed in the MFI membrane structure when removing organic-structure-directing agents in the membrane through calcination at a low temperature using ozone.

BACKGROUND ART

Zeolite is a porous inorganic material having a certain structure and a pore size corresponding thereto, and currently about 200 types of zeolite are known. When a zeolite having a pore size and structure suitable for the material to be separated is selected, a molecular sieve membrane that separates a mixture depending on the size thereof can be produced. For example, an MFI zeolite membrane having a pore size of about 0.55 nm is capable of separating, in a size-dependent manner, a mixture of p-xylene (0.58 nm) and o-xylene (0.68 nm), which are difficult to separate by a conventional distillation-based separation process due to similar boiling points thereof.

Molecular sieve membranes produced using zeolites having micropores are capable of separating mixtures based on size differences and thus exhibit very high separation performance. However, defects are inevitably formed during the process of forming zeolite membranes and during the process of calcination. Defects present in the zeolite membrane deteriorate the performance of the membrane and interfere with the original molecular sieve function of the membrane. In addition, defects are a factor that lowers the separation factor by providing a non-selective path and permeating undesired molecules in addition to the molecules to be separated. Various studies have been continuously reported to obtain a membrane that maximizes the function of the zeolite molecular sieve by minimizing defects. Research on reducing defects that may occur during secondary growth in the process of producing the membrane and during heat-based calcination after the process of producing the membrane, and research on post-treatment methods that reduce defects by introducing an additional process after the production of the membrane are actively conducted in various ways (Zhang et al., Journal of Membrane Science 358 (2010) 7-12; Zhu et al., Microporous and Mesoporous Materials 237 (2017) 140-150; Maghsoudi, Separation & Purification Reviews 45.3 (2016) 169-192; Choi et al., Science 325 (2009) 590-593).

Various techniques for removing defects that lower the separation performance of zeolite membranes have been developed. In particular, defects have been attempted to be reduced by selectively inserting molecules having a larger size than zeolite pores into defects or by accommodating a chemical reaction with organosilanes having a larger size than zeolite pores at the interface between polar and non-polar solvents (Zhang et al., Journal of Membrane Science 358 (2010) 7-12 and Zhang et al., Advanced Functional Materials 18 (2008) 3434-3443). In addition, a method of reducing grain-boundary defects in a zeolite membrane by performing rapid heat treatment prior to calcination to remove organic-structure-directing agents present in the zeolite membrane has also been reported (Choi et al., Science 325 (2009) 590-593). However, these methods require an additional process for the preparation of the zeolite membrane, and in this process, the inherent permeance of the zeolite membrane is often reduced. Research on technology that can effectively control defects in zeolites without requiring an additional process is urgently needed in order to be applicable to actual processes.

Therefore, as a result of extensive efforts to solve these problems, the present inventors demonstrated that, when ozone is included in the gas stream for the process of calcining the MFI membrane, calcination of the organic-structure-directing agents in the pores can be performed at a lower temperature of 100 to 300° C. without an additional process. The resulting zeolite membranes improved xylene isomer separation performance because defects in the membrane that very often occur during high-temperature calcination can be controlled. The present invention has been completed based on this finding.

SUMMARY OF THE INVENTION

Therefore, the present invention has been made in view of the above problems, and it is one objective of the present invention to provide a membrane that has marked p-lo-xylene separation performance without an additional process by controlling defects in the membrane that occur during high-temperature calcination of organic-structure-directing agents of MFI membranes.

It is another objective of the present invention to provide a method for separating xylene isomers using the membrane.

In accordance with an aspect of the present invention, the above and other objectives can be accomplished by the provision of a method of controlling a defect structure in an MFI zeolite membrane, including calcining the MFI zeolite membrane under ozone environment at a temperature of 100 to 300° C.

In accordance with another aspect of the present invention, there is provided a method of separating p-xylene from a mixture of C8 aromatic isomers using the MFI zeolite membrane produced by the method.

BRIEF DESCRIPTION OF THE DRAWINGS

The above and other objectives, features and other advantages of the present invention will be more clearly understood from the following detailed description taken in conjunction with the accompanying drawings, in which.

DETAILED DESCRIPTION OF THE INVENTION

Figure 1:
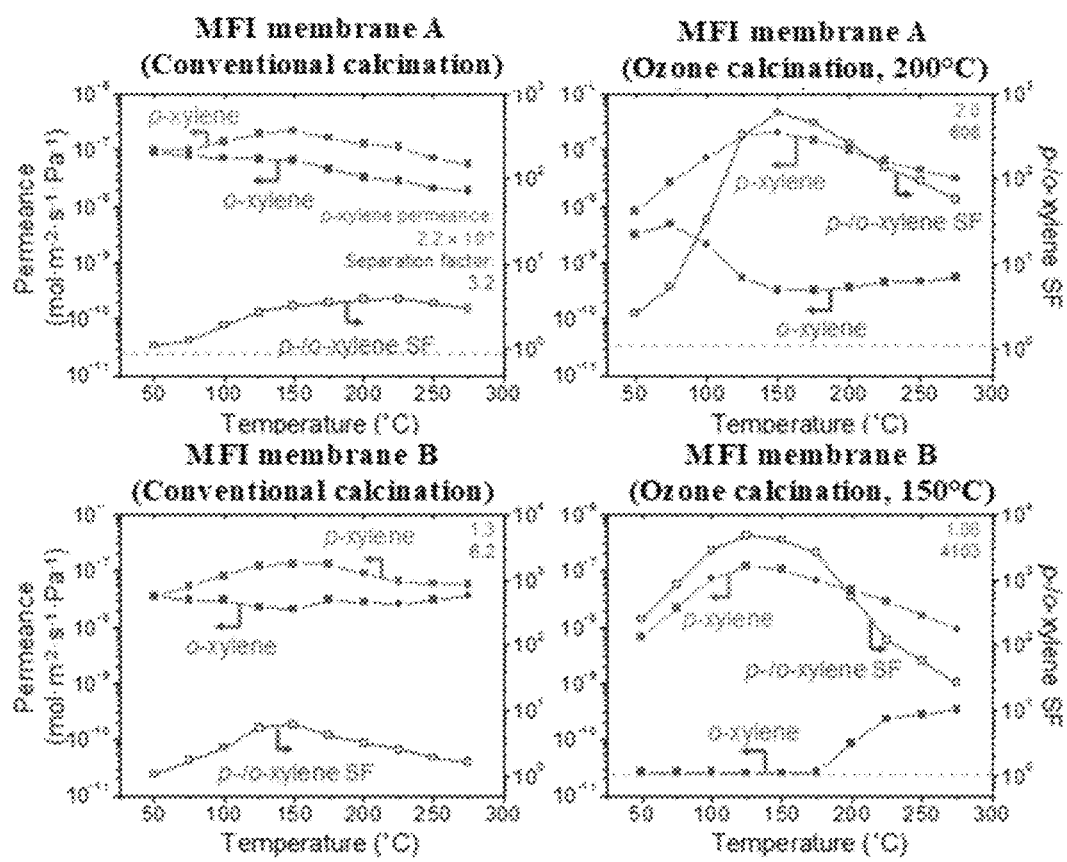
FIG. 1 is a graph showing the performance of separating a p-lo-xylene mixture of MFI membranes A and B depending on conventional calcination and ozone calcination in an embodiment of the present invention.

Unless defined otherwise, all technical and scientific terms used herein have the same meanings as appreciated by those skilled in the field to which the present invention pertains. In general, the nomenclature used herein is well-known in the art and is ordinarily used.

It was found that, when ozone is included in the gas stream for the process of calcining the MFI membrane, the calcination of the organic-structure-directing agents in the pores could be performed at a temperature of 100 to 300° C., which is lower than a conventional calcination process, and thus defects in the membrane occurring during high-temperature calcination could be controlled, and improved p-/o-xylene isomer separation performance was obtained.

Thus, in one aspect, the present invention is directed to a method of controlling a defect structure in an MFI zeolite membrane, including calcining the MFI zeolite membrane under ozone environment at a temperature of 100 to 300° C.

Hereinafter, the present invention will be described in detail.

In general, calcination of the MFI membrane is performed at 480 to 600° C. using air as an oxidizing agent. However, when ozone is included in the gas stream, calcination of the organic-structure-directing agents in the pores can be performed at a much lower temperature (100 to 300° C.) so that defects in the membrane occurring during high-temperature calcination can be controlled. The present invention has an effect of controlling a defect structure, not simply removing the defects of the membrane.

In addition, the present invention provides the calcination conditions of the calcination temperature and time that can exhibit the most effective and optimal xylene isomer separation performance depending on the thickness of the membrane by performing ozone calcination of MFI membranes having various thicknesses, and by controlling and analyzing the defect structures in the membrane. In this case, defects in the membranes subjected to ozone calcination were identified through FCOM (fluorescence confocal optical microscopy) analysis. When the MFI membrane A was calcined with ozone, defects in the form of dots were formed at a low density rather than connected defects as in conventional calcination. In addition, the MFI membrane B was found to have defects in the form of cracks having a large size when subjected to conventional calcination. However, when ozone calcination was performed, grain-boundary defects having a small size were formed. MFI membrane A is an MFI membrane having a thickness of 1 to 2 μm after hydrothermal synthesis at 90° C. for 5 days, and MFI membrane B is an MFI membrane having a thickness of 4 to 6 μm after hydrothermal synthesis at a temperature of 140° C. for 1 day.

In the present invention, the calcination of the organic-structure-directing agent in the pores is performed at a very low temperature of 100 to 300° C., preferably 150 to 275° C., so that defects in the membrane occurring during high-temperature calcination can be controlled.

In the present invention, controlling the defect structure of the zeolite membrane or controlling the defects in the membrane means reducing the number and size of defects present in the membrane, wherein the size of the defects having 4 to 10 nm can be reduced to 2 nm or less, preferably to 1 nm or less. According to a specific embodiment of the present invention, defects having a size of 4 to 5 nm or 8 to 10 nm can be reduced to 1 nm or less.

In the present invention, ozone may be fed in total amount of 0.05 to 75 vol % at a rate of ozone feeding of 0.001 to 1.5 g/min, and calcination may be conducted at a temperature increase rate of 0.1 to 20° C./min for 0.5 to 168 hours. In addition, ozone and oxygen may be fed together.

In the present invention, the MFI zeolite membrane may be produced by adding a secondary growth solution containing an organic-structure-directing agent, $SiO_2$, $H_2O$, $Al_2O_3$ and $Na_2O$ at a molar ratio of 1 to 100:5 to 500:1,000 to 50,000:0 to 100:0 to 1,000 to a support, on which an MFI seed layer is formed, and then conducting hydrothermal synthesis.

In the present invention, the organic-structure-directing agent may include at least one selected from the group consisting of TPAOH (tetrapropylammonium hydroxide), TPABr (tetrapropylammonium bromide), TPAF (tetrapropylammonium fluoride), TPACl (tetrapropylammonium chloride), TPAI (tetrapropylammonium iodide), TEAOH (tetraethylammonium hydroxide), TEABr (tetraethylammonium bromide), TEAF (tetraethylammonium fluoride), TEACl (tetraethylammonium chloride), and TEAI (tetraethylammonium iodide). Preferred is the use of TPAOH, but the present invention is not limited thereto.

In the present invention, the hydrothermal synthesis may be performed at a temperature of 80 to 200° C. for 12 to 240 hours, preferably at a temperature of 90 to 140° C. for 24 to 240 hours. When the hydrothermal synthesis is performed under the temperature and time conditions satisfying the ranges defined above, there is an effect in that a continuous MFI membrane can be synthesized because the gaps in the MFI seed layer are densely filled through hydrothermal synthesis.

In the present invention, the hydrothermal synthesis may be performed once or twice, but is not limited thereto.

In the present invention, the method may further include, after the hydrothermal synthesis, drying the membrane at a temperature of 30 to 200° C. for 1 to 24 hours, preferably at a temperature of 50 to 100° C. for 5 to 12 hours.

In the present invention, the support may include at least one selected from the group consisting of alpha-alumina, polypropylene, polyethylene, polytetrafluoroethylene, polysulfone, polyimide, silica, glass, gamma-alumina, mullite, zirconia, titania, yttria, ceria, vanadia, silicon, stainless steel and carbon, but is not limited thereto.

The result of measurement of the separation performance of the p-xylene/o-xylene mixture using the MFI zeolite membrane produced in an embodiment of the present invention showed that when ozone calcination is performed, the p-xylene of the MFI zeolite membrane exhibited excellent permeance and separation factor, compared to conventional calcination.

Thus, in another aspect, the present invention is directed to a method of separating p-xylene from a mixture of C8 aromatic hydrocarbons containing xylene isomers using the MFI zeolite membrane produced by the method.

The size of the MFI zeolite pores according to the present invention is about 0.55 nm, which is similar to that of p-xylene (0.58 nm) and is smaller than that of o-xylene (0.68 nm). Therefore, a mixture of C8 aromatic isomers can be separated based on size differences using a membrane. The ozone-calcined MFI zeolite membrane can control the amount and size of defects in the membrane and thus has the minimum defects suitable for the separation process, thereby obtaining higher separation performances.

In the present invention, the C8 aromatic isomer may be p-xylene (0.58 nm), m-xylene (0.68 nm), o-xylene (0.68 nm), or ethylbenzene (0.60 nm).

In addition, in the present invention the MFI membrane-based xylene separation can be carried out at a temperature of 50° C. or higher, preferably 100° C. or higher, more preferably 100 to 400° C., and even more preferably 100 to 275° C.

Hereinafter, the present invention will be described in more detail with reference to examples. However, it will be obvious to those skilled in the art that these examples are provided only for illustration of the present invention and should not be construed as limiting the scope of the present invention.

EXAMPLE

Example 1: Production of MFI Particles

In order to synthesize MFI particles to be used as seeds for synthesizing the membrane, particles having a size of about 100 nm were obtained using a previously reported method (Choi et al., Adsorption, 2006, 12, 339-360). The obtained particles were deposited on a support to form a seed layer. The uniformly formed MFI zeolite seed layer was subjected to hydrothermal synthesis to form a membrane on the support.

Example 2: Production of MFI Membrane Through Secondary Growth

A secondary growth solution was produced using TPAOH, an organic-structure-directing agent used for synthesis of MFI particles, for secondary growth (Choi et al., Adsorption, 2006, 12, 339-360). The seed layer was added to the prepared solution and hydrothermal synthesis for secondary growth was conducted to obtain an MFI zeolite membrane. At this time, the secondary growth was performed under two conditions. Hydrothermal synthesis was performed at a temperature of 90° C. for 5 days to synthesize an MFI membrane A having a thickness of 1 to 2 µm, and hydrothermal synthesis was performed at a temperature of 140° C. for 1 day to synthesize an MFI membrane B having a thickness of 4 to 6 µm.

Example 3: Conventional Calcination and Ozone Calcination of MFI Membrane

After synthesizing MFI membranes A and B, calcination was performed through two methods. First, conventional calcination was performed at 480° C. for 10 hours while feeding air at 200 cc/min. At this time, the rate of temperature increase to 480° C. was maintained at 0.5° C./min. Second, ozone calcination was performed at 100 to 300° C. for 12 hours. Ozone was produced through an ozone generator. At this time, oxygen was fed at a rate of 1 L/min and a total of 0.1 g/min (5 vol %) of ozone was fed into the membrane during calcination. At this time, the rate of temperature increase to 100-300° C. was maintained at 0.5° C./min.

Example 4: Determination of Separation Performance of Xylene Mixture

The MFI membrane A and the MFI membrane B were synthesized, and they were subjected to conventional calcination and ozone calcination. The resulting separation performance of the p-xylene/o-xylene mixture is shown in FIG. 1. The conventionally calcined MFI membrane A had a p-xylene permeance of $2.2 \times 10^{-7}$ mol·m$^{-2}$·s$^{-1}$·Pa$^{-1}$ and a p-xylene/o-xylene separation factor (p-lo-xylene SF) of 3.2 at 150° C. However, when ozone calcination was performed at 200° C. for 12 hours, a p-xylene permeance of $2.0 \times 10^{-7}$ mol·m s$^{-1}$·Pa$^{-1}$ and a p-lo-xylene SF of 608 at 150° C. were obtained. The conventionally calcined MFI membrane B exhibited a p-xylene permeance of $1.3 \times 10^{-7}$ mol·m$^{-2}$·s$^{-1}$·Pa$^{-1}$ and a p-lo-xylene SF of 6.2 at 150° C. However, when ozone calcination was performed at 150° C. for 12 hours, the p-xylene permeance of $1.06 \times 10^{-7}$ mol·m$^{-2}$·s$^{-1}$·Pa$^{-1}$ and a p-lo-xylene SF of 4,103 at 150° C. were obtained.

Figure 2:
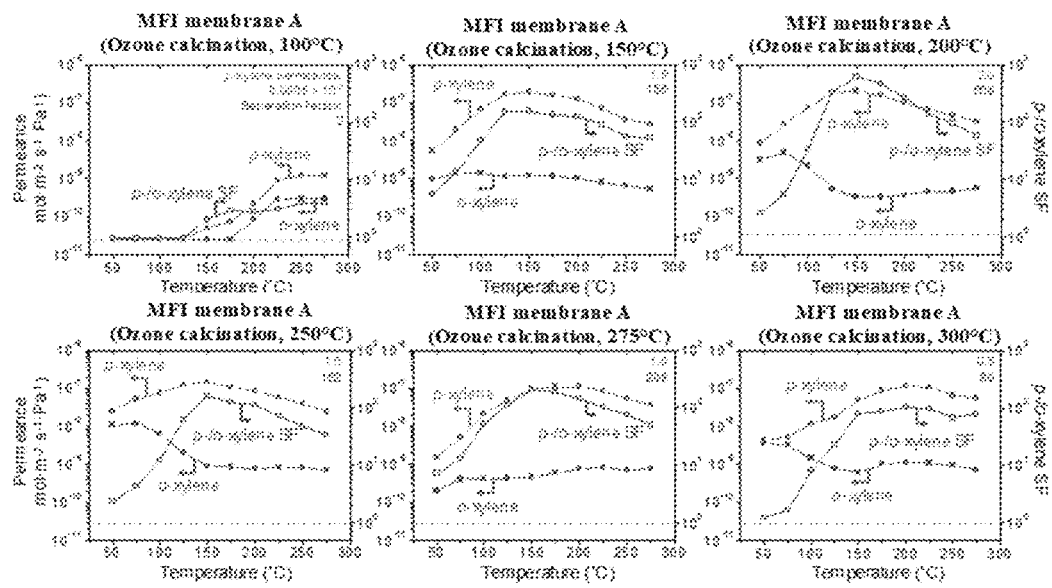
FIG. 2 is a graph showing the performance of separating a p-lo-xylene mixture of the MFI membrane A depending on the ozone calcination temperature in an embodiment of the present invention.
Figure 3:
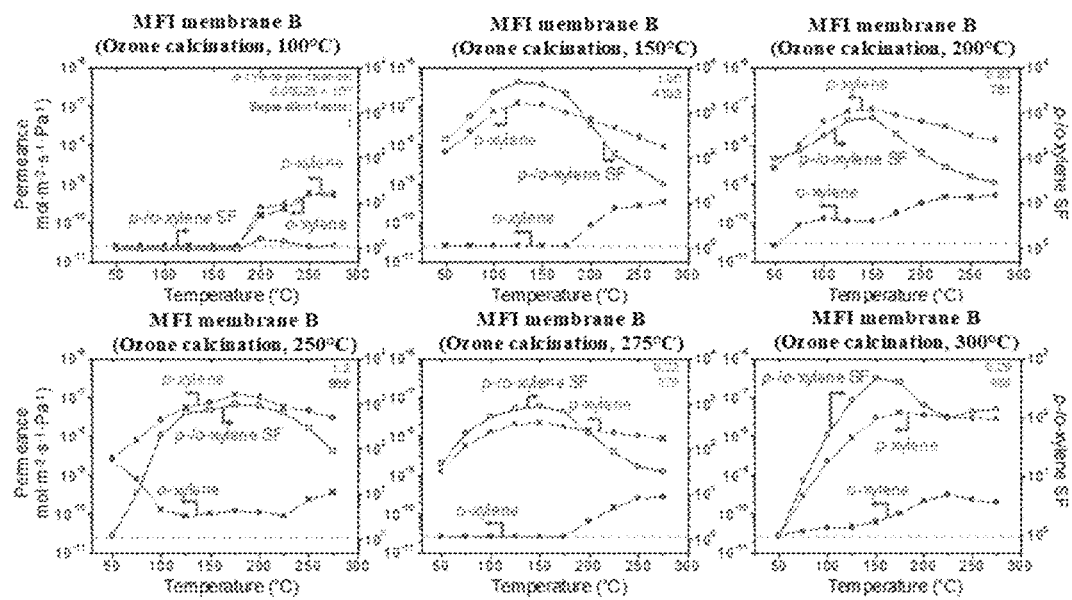
FIG. 3 is a graph showing the performance of separating a p-/o-xylene mixture of MFI membrane B depending on ozone calcination temperature in an embodiment of the present invention.

In addition, the separation performance of the p-lo-xylene mixture of MFI membrane A depending on the ozone calcination temperature in the range of 100 to 300° C. was measured and is shown in FIG. 2, and the separation performance of the p-lo-xylene mixture of MFI membrane B subjected to different ozone calcination temperature was measured and is shown in FIG. 3.

In both MFI membranes A and B, organic-structure-inducing agents in the membrane were not sufficiently removed through ozone calcination at 100° C., resulting in very low xylene permeance and separation factor. However, the organic-structure-inducing agents in the membrane were sufficiently removed through ozone calcination conducted at 150 to 250° C., and the MFI membrane A exhibited p-xylene permeance at 150° C. of 1.5 to $2.0 \times 10^{-7}$ mol·m$^{-2}$·Pa$^{-1}$ and MFI membrane B exhibited p-xylene permeance at 150° C. of 0.8 to $1.2 \times 10^{-7}$ mol·m$^{-2}$·s$^{-1}$·Pa$^{-1}$. In addition, the MFI membrane A exhibited a p-lo-xylene SF at 150° C. of 150 to 600 and the MFI membrane B exhibited a p-lo-xylene SF at 150° C. of 700 to 4,100. It can be seen that the separation factor obtained through ozone-calcined MFI membranes is very high, especially taking into account that the separation factor of the conventionally calcined MFI membranes is 3 to 6.

Figure 4:
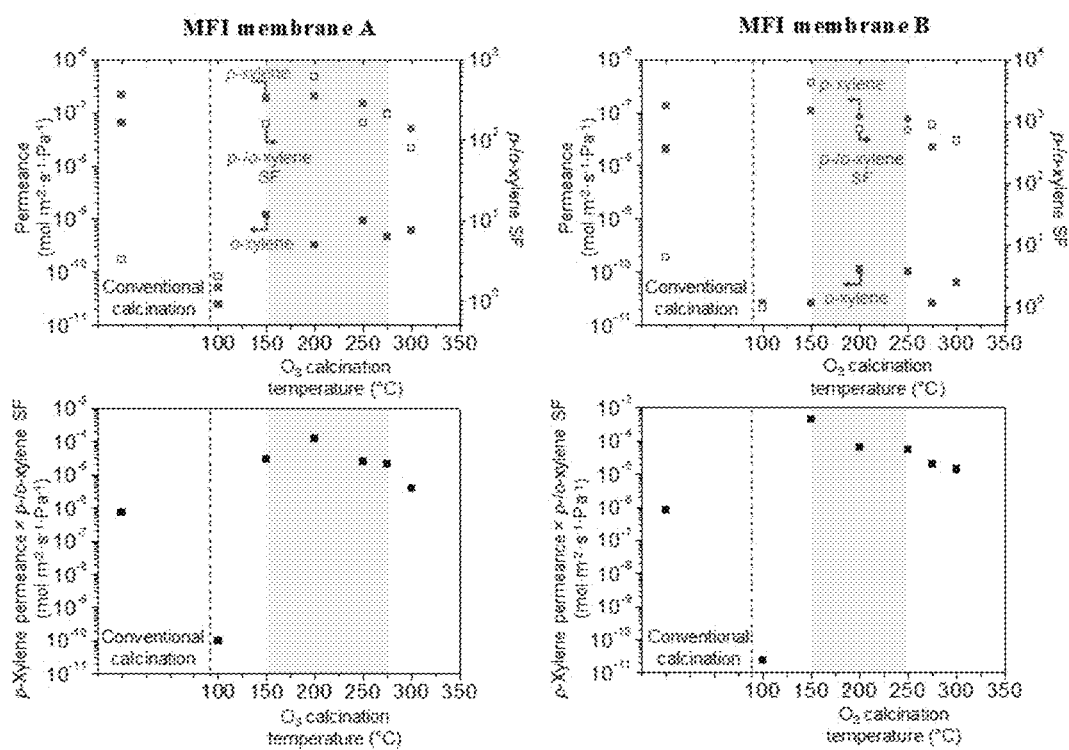
FIG. 4 is a graph showing a change in separation performance of MFI membranes A and B depending on conventional calcination and ozone calcination temperatures in an embodiment of the present invention.

The permeances of p-xylene and o-xylene, and p-lo-xylene separation factors of MFI membranes A and B depending on conventional calcination and ozone calcination temperatures are summarized in FIG. 4. In addition, in FIG. 4, in order to accurately compare the performance changes of the membranes, the values obtained by multiplying the permeance of p-xylene and the p-lo-xylene separation factor were compared between the membrane subjected to conventional calcination and the membrane subjected to ozone calcination at each temperature. When comparing the values of the permeance of p-xylene x p-lo-xylene separation factor, it can be seen that the membranes ozone-calcined at 100° C. had very low values, but the MFI membrane A had a very high value upon ozone calcination at 150 to 275° C., and the MFI membrane B had a very high value upon ozone calcination at 150 to 250° C. In addition, it can be seen that these values are significantly improved especially when compared to the values of the membranes subjected to conventional calcination.

Example 5: Determination of a Defect Structure of MFI Membranes

Figure 5:
FIG. 5 is a fluorescence confocal optical microscopic image of MFI membranes A and B depending on conventional calcination and ozone calcination in an embodiment of the present invention.
Figure 5:
Figure 5:
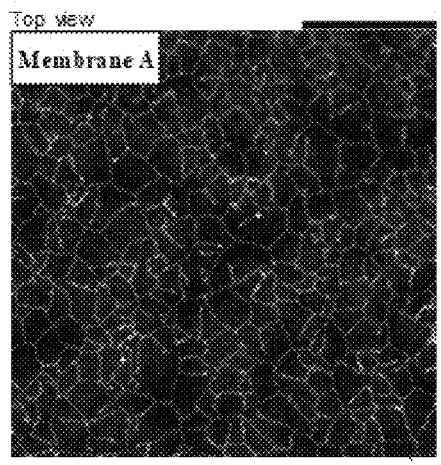
Figure 5:
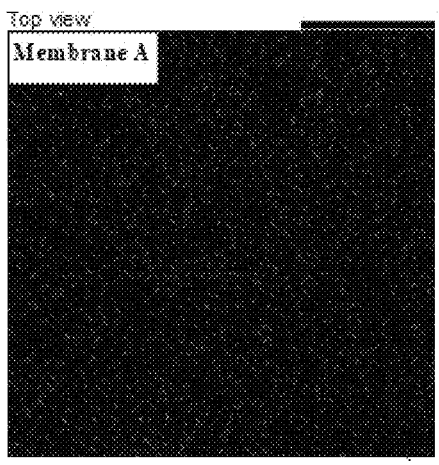
Figure 5:
Figure 5:
Figure 5:
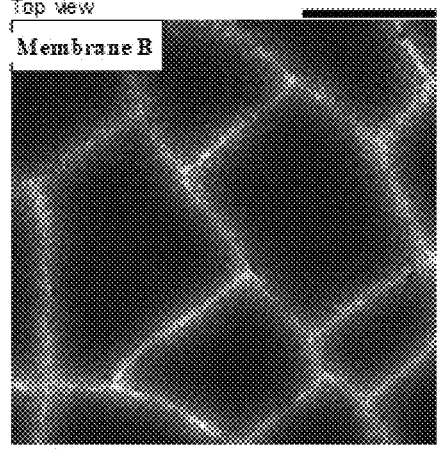
Figure 5:
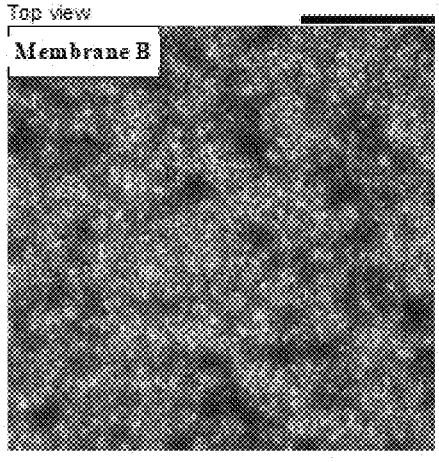

In order to determine the defect characteristics of the MFI membranes A and B produced by the method of Examples 1 to 3, FCOM measurement was performed. When dyeing the membrane using a dye molecule having a size of ~1 nm, defects having a size of 1 nm or more in the membrane can be selectively detected by FCOM. Through this, the structure of defects in the membrane can be observed. The defect structures of the MFI membrane produced by ozone calcination and the MFI membrane produced by conventional calcination were disclosed by FCOM and are shown in FIG. 5. FCOM analysis indicates that the defects of the conventionally calcined MFI membrane A were distributed throughout the membrane. However, when the MFI membrane A was ozone-calcined, defects in the form of dots were formed at a low density rather than connected defects as in conventional calcination. In addition, it was found that the conventionally calcined MFI membrane B had defects in the form of cracks having a large size. However, the ozone-calcined MFI membrane B had grain-boundary defects having a small size.

Figure 6:
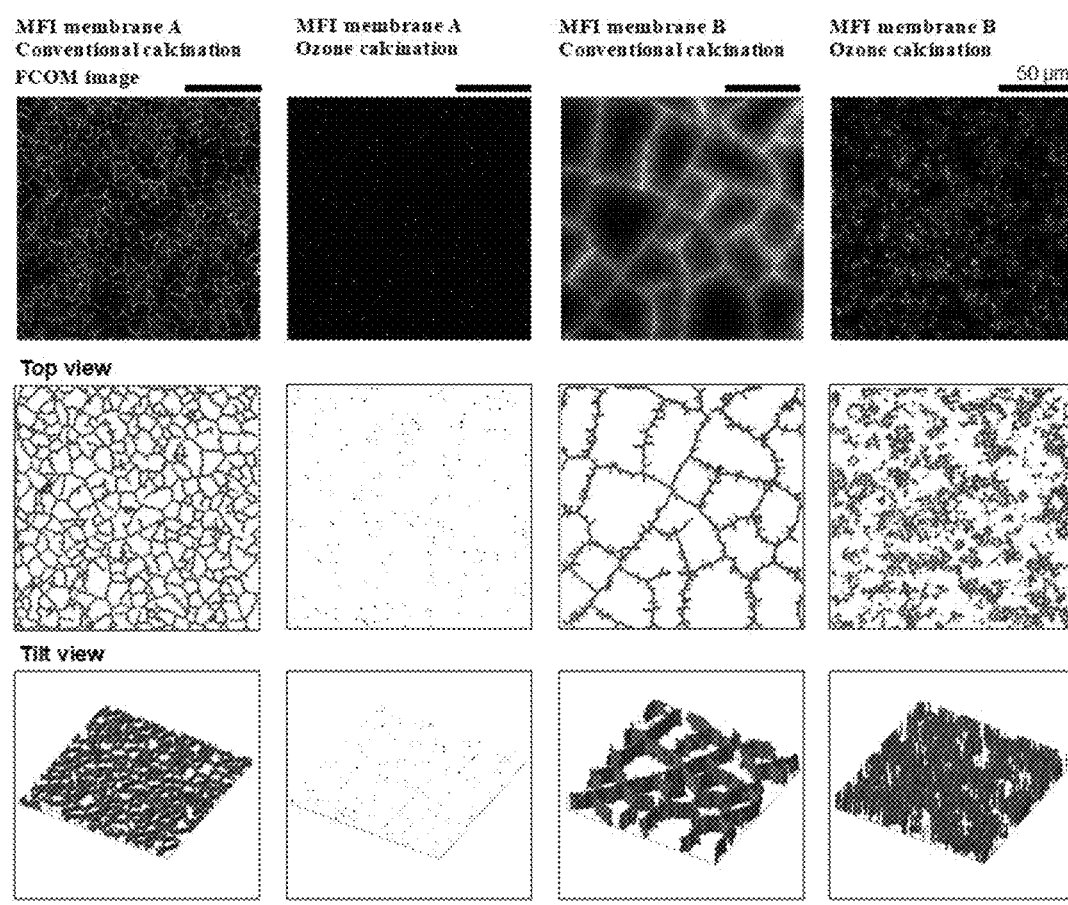
FIG. 6 is an image showing defects obtained through image processing of the fluorescence confocal optical microscopic image of MFI membranes A and B depending on conventional calcination and ozone calcination in an embodiment of the present invention.

Defects in the membranes were quantitatively analyzed through image processing of the FCOM images of MFI membranes A and B. First, defects obtained through image processing in the FCOM images of MFI membranes A and B are schematically shown in FIG. 6.

Quantitative features (tortuosity and area fractions) can be obtained based on the data of defects extracted through image processing, and the defect size and porosity of each membrane can be obtained by complementing the quantitative features with the 1-D permeation model. The relevant properties are summarized in Table 1.

TABLE 1

Defect structure characteristics of MFI membranes depending on conventional calcination and ozone calcination.

| Sample | Calcination method | Tortuosity (z-direction) | Area fraction | Defect size (nm) | Porosity (%) |
| --- | --- | --- | --- | --- | --- |
| MFI membrane A | Conventional calcination | 1.45 | $4.24 \times 10^{-2}$ | 4~5 | 0.23~0.26 |
| MFI membrane A | Ozone calcination | 1.94 | $4.28 \times 10^{-3}$ | N/A | N/A |
| MFI membrane B | Conventional calcination | 1.74 | $1.62 \times 10^{-2}$ | 8~10 | 0.17~0.2 |
| MFI membrane B | Ozone calcination | 1.42 | $7.57 \times 10^{-2}$ | 1 | 0.09 |

When comparing the result of conventional calcination of MFI membrane A with the result of ozone calcination thereof, the pixel-based area fractions of defects in the two membranes differ by about 10 times. This is because the FCOM image of the ozone-calcined MFI membrane A has a scattered spot shape rather than a continuous crack shape. The result of the quantitative analysis showed that the conventionally calcined MFI membrane A had a defect size of 4 to 5 nm, but when ozone calcination was performed, the defect decreased to a size of 1 nm or less that cannot be detected as a dyed molecule.

When comparing the result of the conventional calcination of the MFI membrane B with the result of the ozone calcination thereof, the membrane that has undergone conventional calcination has crack-shaped defects having a large size. The result of quantitative analysis showed that the size of large cracks seen in the conventionally calcined membrane was 8 to 10 nm. Considering that the size of the small defects in the ozone-calcined membrane is 1 nm, which is similar to the size of the dye molecule, it was found that the size of the defects decreased by ~10 times through ozone calcination.

INDUSTRIAL APPLICABILITY

The present invention provides a method capable of controlling the size and amount of defects in the membrane formed during calcination in the process of producing the zeolite membrane. The method is capable of reducing the amount and size of defects formed in the high-temperature process by performing calcination at a low temperature compared to a conventional calcination method.

In the present invention, a method of calcining an organic-structure-directing agent in a membrane at a low temperature under ozone environment was used. The amount and size of defects in the membrane can be controlled by controlling the temperature and time at which ozone-based calcination is performed. As a result, a membrane having the least defects suitable for the separation process can be produced.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A method of controlling a defect structure in an MFI zeolite membrane comprising:
   preparing a precursor MFI zeolite membrane by adding a mixture of a secondary growth solution containing an organic-structure-directing agent, $SiO_2$, $H_2O$, $Al_2O_3$ and $Na_2O$ to a support, on which an MFI seed layer is formed, and conducting hydrothermal synthesis for the mixture on the support at a temperature of 80 to 200° C. for 12 to 240 hours;
   drying the precursor MFI zeolite membrane at a temperature of 30 to 200° C. for 1 to 24 hours; and
   calcining the dried precursor MFI zeolite membrane under ozone environment at a temperature of 150 to 275° C.

2. The method of controlling a defect structure in an MFI zeolite membrane of claim 1, wherein, in the calcining step, ozone in the ozone environment is fed in a total amount of 0.05 to 75 vol % at a rate of ozone feeding of 0.001 to 1.5 g/min, and the calcining is conducted at a temperature increase rate of 0.1 to 20° C./min for 0.5 to 168 hours.

3. The method of controlling a defect structure in an MFI zeolite membrane of claim 1, wherein a molar ratio of the organic-structure-directing agent, the $SiO_2$, the $H_2O$, the $Al_2O_3$ and the $Na_2O$ is 1 to 100:5 to 500:1,000 to 50,000: more than 0 to at or below 1000:more than 0 to at or below 1,000.

4. The method of controlling a defect structure in an MFI zeolite membrane of claim 1, wherein the organic-structure-directing agent is at least one selected from the group consisting of TPAOH (tetrapropylammonium hydroxide), TPABr (tetrapropylammonium bromide), TPAF (tetrapropylammonium fluoride), TPACl (tetrapropylammonium chloride), TPAI (tetrapropylammonium iodide), TEAOH (tetraethylammonium hydroxide), TEABr (tetraethylammonium bromide), TEAF (tetraethylammonium fluoride), TEACl (tetraethylammonium chloride) and TEAI (tetraethylammonium iodide).

5. The method of controlling a defect structure in an MFI zeolite membrane of claim 1, wherein the support is at least one selected from the group consisting of alpha-alumina, polypropylene, polyethylene, polytetrafluoroethylene, polysulfone, polyimide, silica, glass, gamma-alumina, mullite, zirconia, titania, yttria, ceria, vanadia, silicon, stainless steel and carbon.

* * * * *